(12) United States Patent
Gostelow

(10) Patent No.: US 7,328,702 B2
(45) Date of Patent: Feb. 12, 2008

(54) TRACHEOSTOMY DEVICE

(75) Inventor: Thomas Gostelow, Springhead (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 10/549,617

(22) PCT Filed: Apr. 21, 2004

(86) PCT No.: PCT/GB2004/001707

§ 371 (c)(1),
(2), (4) Date: Sep. 20, 2005

(87) PCT Pub. No.: WO2004/096331

PCT Pub. Date: Nov. 11, 2004

(65) Prior Publication Data

US 2006/0081254 A1    Apr. 20, 2006

(30) Foreign Application Priority Data

Apr. 25, 2003 (GB) .................................. 0309389.5

(51) Int. Cl.
*A61M 11/00* (2006.01)
(52) U.S. Cl. .............................. 128/207.16; 128/207.29
(58) Field of Classification Search ........... 128/200.26, 128/207.14, 207.15, 207.16, 207.29; 604/93.01, 604/95.03, 95.04, 164.04, 104, 105, 106, 604/107, 108, 109, 174, 175
See application file for complete search history.

(56) References Cited

U.S. PATENT DOCUMENTS

| | | | | |
|---|---|---|---|---|
| 3,889,688 A | * | 6/1975 | Eamkaow | 128/207.15 |
| 4,278,081 A | * | 7/1981 | Jones | 128/207.15 |
| 4,471,782 A | * | 9/1984 | Shuffield | 606/197 |
| 4,516,578 A | * | 5/1985 | Shuffield | 604/514 |
| 5,056,515 A | * | 10/1991 | Abel | 128/207.15 |
| 5,123,922 A | * | 6/1992 | Berg | 623/9 |
| 5,287,852 A | * | 2/1994 | Arkinstall | 128/207.14 |
| 5,638,813 A | * | 6/1997 | Augustine | 128/207.15 |
| 5,738,654 A | * | 4/1998 | Tihon | 604/105 |
| 5,771,888 A | * | 6/1998 | Keim | 128/207.15 |
| 6,527,737 B2 | * | 3/2003 | Kaneshige | 604/48 |
| 6,840,242 B1 | * | 1/2005 | McCoy | 128/207.14 |

* cited by examiner

*Primary Examiner*—Steven O. Douglas
(74) *Attorney, Agent, or Firm*—Louis Woo

(57) ABSTRACT

A tracheostomy device has a short tube terminating adjacent the internal end of an opening into the trachea. A flange secures the external end of the tube and a retainer secures the internal end of the tube against the surface of the trachea. The device also includes a seal, which engages the surface of the trachea above the opening, and a suction passage extending externally by which secretions can be removed.

10 Claims, 2 Drawing Sheets

TRACHEOSTOMY DEVICE

BACKGROUND OF THE INVENTION

This invention relates to tracheostomy devices of the kind including a tubular member adapted to provide a gas passage into the trachea through an opening in neck tissues and an external retainer for retaining the tubular member with the external surface of the neck adjacent the opening.

FIELD OF INVENTION

A tracheostomy is used to enable direct access for breathing gases into the trachea through a surgically-made opening in the throat. The airway into the trachea is usually maintained with a tracheostomy tube. The tracheostomy tube has a patient end angled so that its axis is directed generally caudally along the trachea. The tube is bent along its length so that the machine end emerges through the tracheostomy and is terminated by a coupling and a flange to which a strap is secured. The strap extends about the neck of the patient and is used to hold the tube in position. Tracheostomy tubes often have an inflatable cuff close to the patient end, which seals with the inside of the trachea, so as to confine gas flow to the bore of the tube. Tracheostomy tubes may have fenestrations above the cuff to allow some air flow to the larynx and thereby enable the patient to speak.

Tracheostomy tubes have been used satisfactorily for many years. However, they do suffer from a number of disadvantages. First, during use, secretions build up on the inside of the tube, which provide a site for the accumulation of bacteria. Release of these secretions into the respiratory passages is thought to be associated with a high prevalence of pneumonia infection in ventilated patients. For this reason, tracheostomy tubes must be carefully cleaned regularly. Alternatively, the tube may have a liner or inner cannula that is periodically removed and disposed of. These inner cannula have their own problems, such as in reducing the bore through the tracheostomy tube. The maintenance necessary for tracheostomy tubes is an additional burden on hospital staff and requires the establishment of procedures to ensure that the maintenance is carried out correctly and routinely. Another problem with tracheostomy tubes is that they need to be secured to the neck by means of a strap or the like. This makes the tubes more conspicuous, which is a particular problem to patients where the tube needs to be in place for prolonged periods. A further problem arises with cuffed tubes in that secretions produced in the upper part of the trachea, above the cuff on the tube, tend to collect on the inflated cuff, between the outside of the tube and the trachea. Although some of these secretions can be removed by suctioning, it is difficult to remove all secretions from the confined space between the tube and trachea.

It is an object of the present invention to provide an alternative tracheostomy device.

SUMMARY OF INVENTION

According to one aspect of the present invention there is provided a tracheostomy device of the above-specified kind, characterised in that the patient end of the tubular member terminates adjacent the internal end of the opening, and that the device includes an internal retainer for retaining the tubular member with the internal surface of the trachea adjacent the opening.

The device preferably includes a seal for substantially sealing the trachea above the opening into the trachea. The seal may have a fluid passage, such as a suction passage, opening at one end above the seal and extending out of the trachea via the opening. The seal preferably includes a deformable annular ring arranged to engage the surface of the trachea. The annular ring may be inflatable or it may include a resilient foam. The seal may include a web extending across the ring. The external retainer is preferably a flange and the internal retainer may be a displaceable member, such as a hinged tab and the tab may be connected with a cord by which the tab can be displace.

According to a second aspect of the present invention there is provided a tracheostomy device comprising a tubular member adapted to provide a gas passage into the trachea through an opening in neck tissues and a seal joined with the tubular member, characterised in that the seal is adapted to seal the trachea above the opening and retain the tubular member in position.

According to a third aspect of the present invention there is provided a method of enabling flow of gas to a patient's trachea including the steps of forming a gas passage through neck tissue into the trachea and sealing the trachea against gas flow at a location above the gas passage.

BRIEF DESCRIPTION OF DRAWINGS

A tracheostomy device according to the present invention will now be described, by way of example, with reference to the accompanying drawings, in which.

DETAILED DESCRIPTION OF INVENTION

Figure 1:
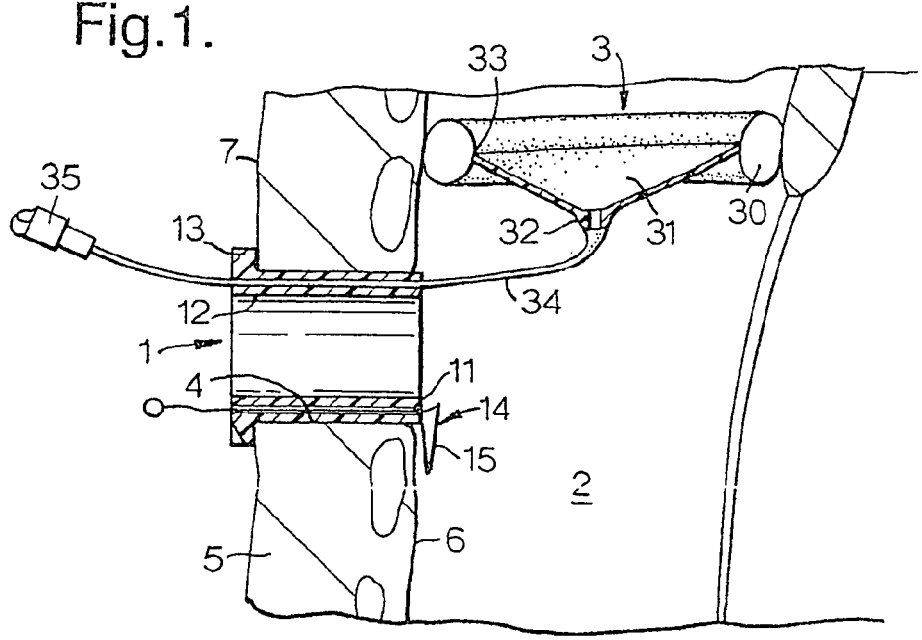
FIG. 1 is a sectional side elevation view of the device in use.
Figure 2:
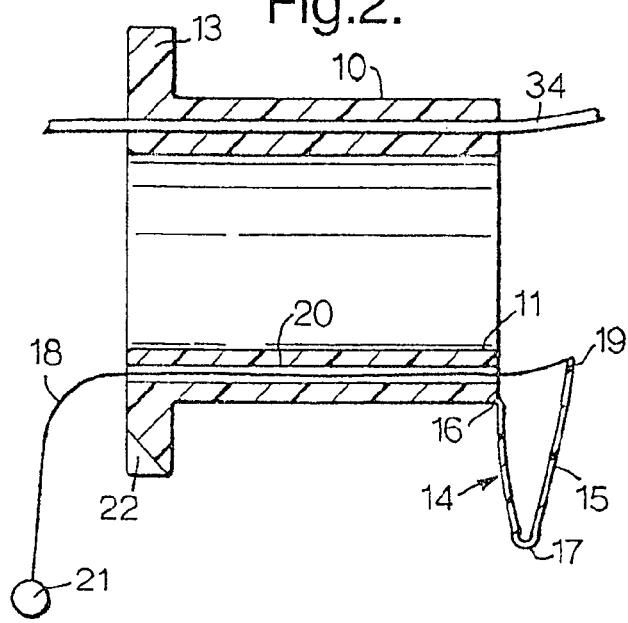
FIG. 2 is a sectional side elevation view of a part of the device to a larger scale.
Figure 3:
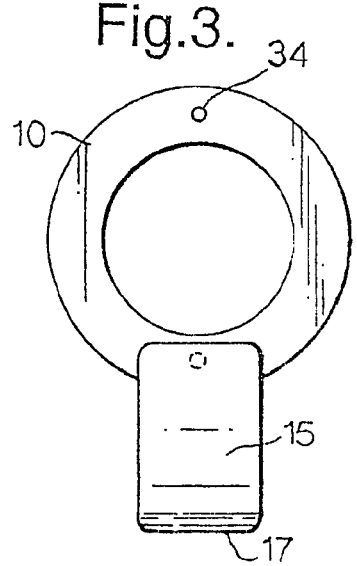
FIG. 3 is a end view of the patient end of the part shown in FIG. 2.

With reference first to FIGS. 1 to 3, the device comprises two components namely a tubular component 1 providing an airway into the trachea 2 and a seal 3 preventing flow of gas along the trachea.

The tubular component 1 comprises a short, stiff, plastics tube 10 of circular section. The tube 10 extends through a tracheostomy opening 4 through neck tissue 5 overlying the trachea 2 and its length is selected so that its patient end 11 terminates adjacent the internal end of the opening and its machine end 12 lies closely adjacent the skin surface 7.

Both the machine end 12 and the patient end 11 have some form of retaining means 13 and 14 respectively to prevent displacement of the tube 10. The external retaining means at the machine end 12 takes the form of a fixed circular flange 13 projecting radially outwardly and abutting the skin surface 7 around the opening 4. The flange 13 may be clear or skin-coloured to make it less conspicuous. The machine end 12 of the tube 10 may include The short length of the tube 10, without any appreciable projection into the trachea 2, has several advantages. There is less accumulation of secretions so maintenance is greatly facilitated. There is less risk of blockage by obstructions within the tube 10 and there is no risk of blocking by contact with the carina. The tube 10 affords less resistance to gas flow than conventional, longer tubes. Also, the short tube 10 does not create any obstruction should surgery be needed within the trachea 2 just below the tracheostomy 4. The absence of a cuff contacting the trachea below the tracheostomy opening can be an advantage if there has been damage to the trachea in this region. Because the tube 10 can be securely retained by the internal and external retaining means, there is less need to use a strap to secure the external flange around the neck. This can help make the device less conspicuous than conventional tracheostomy tubes.

Various modifications are possible to the device. The tube could be adjustable in length, such as by screw threading.

Figure 4:
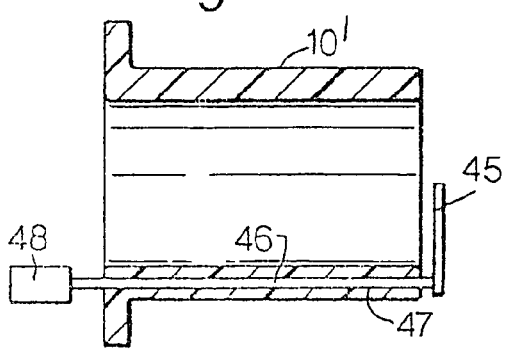
FIG. 4 is a sectional side elevation view of a part of an alternative device.
Figure 5:
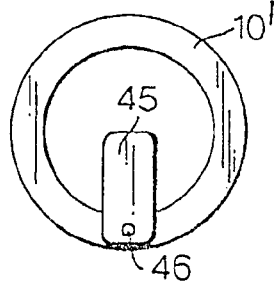
FIG. 5 is an end view of the patient end of the part shown in FIG. 4.

Many alternative forms of retaining means are possible. FIGS. 4 and 5 show a tube 10' with an inner retaining means provided by a rotatable tab 45 mounted on one end of a shaft 46 that extends outwardly through a lumen 47 in the wall of the tube. By rotating a handle 48 on the external end of the shaft, the tab 45 can be swung from a first position where it projects inwardly (for insertion) to a second position where it projects outwardly (for retaining the tube).

Figure 6:
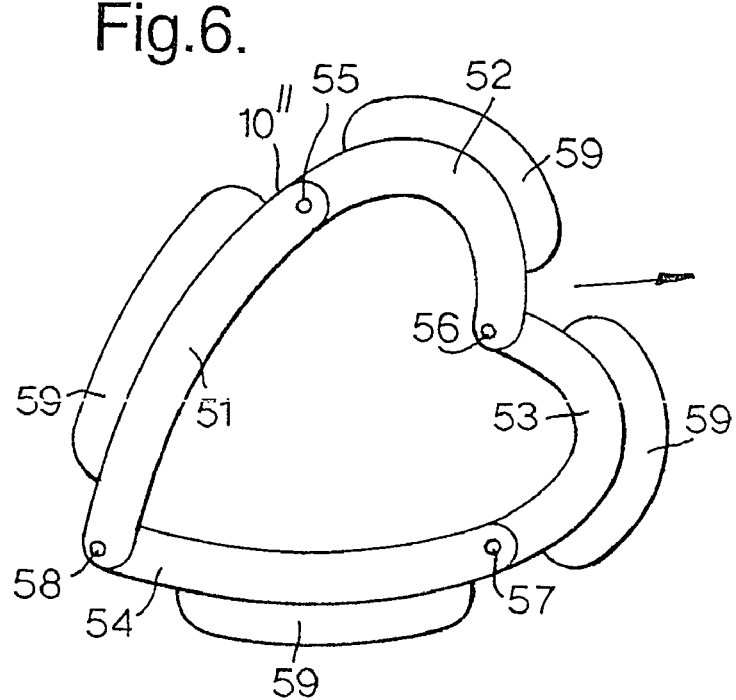
FIG. 6 is a cross-sectional view of a part of another alternative device.

FIG. 6 illustrates a tube 10" in four longitudinal sections 51 to 54 that are foldable with one another along four longitudinal hinge lines 55 to 58 and that has fixed flanges 59 at both ends. The tube 10" is collapsed to a smaller cross-section for insertion so that the inner flanges 59 do not hinder this. The tube 10" is then opened out within the tracheostomy opening so that the flanges 59 at the ends engage the surface of the trachea and the skin respectively.

Figure 7:
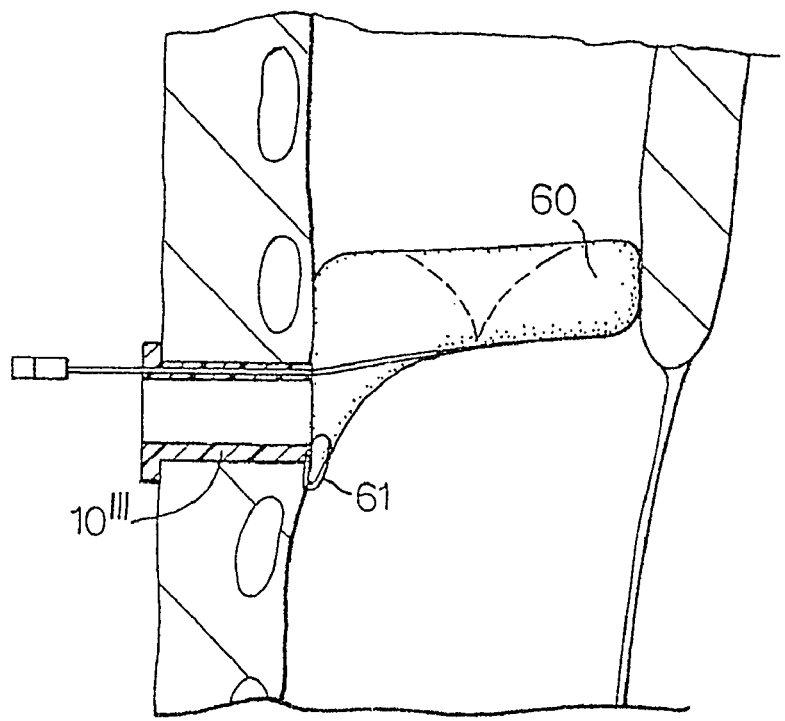
FIG. 7 is a sectional side elevation view of a further alternative device in use.

FIG. 7 illustrates an alternative device where the inner retaining means is provided by the same component that effects the sealing. A deformable sealing ring 60 located above

The invention claimed is:

1. A tracheostomy device including a tubular member adapted to provide a gas passage into the trachea through an opening in neck tissues and an external retainer for retaining the tubular member with the external surface of the neck adjacent the opening, characterized in that the patient end of the tubular member terminates adjacent the internal end of the opening without extending below the opening, and that the device includes an internal retainer for retaining the tubular member with the internal surface of the trachea adjacent the opening and a gas seal located in the trachea above the opening with a lower side exposed to gas pressure within the trachea and substantially sealing the trachea above the opening against the flow of gas along the trachea in either direction such that gas flow to and from the trachea is confined to the tubular member.

2. A tracheostomy device according to claim 1, characterized in that the seal includes a fluid passage opening at one end of the seal and extending out of the trachea via the opening.

3. A tracheostomy device according to claim 2, characterized in that the fluid passage is a suction passage.

4. A tracheostomy device according to claim 1, characterized in that the seal includes a deformable annular ring arranged to engage the surface of the trachea.

5. A tracheostomy device according to claim 4, characterized in that the annular ring is inflatable.

6. A tracheostomy device according to claim 4, characterized in that the annular ring includes a resilient foam.

7. A tracheostomy device according to claim 4, characterized in that the seal includes a web extending across the ring.

8. A tracheostomy device according to claim 1, characterized in that the external retainer is a flange and that the internal retainer is a displaceable member.

9. A tracheostomy device according to claim 8, characterized in that the displaceable member is a hinged tab, and that the tab is connected with a cord by which the tab can be displaced.

10. A tracheostomy device including a tubular member adapted to provide a gas passage into the trachea through an opening in neck tissues and an external retainer for retaining the tubular member with the external surface of the neck adjacent the opening characterized in that the patient end of the tubular member terminates adjacent the internal end of the opening, that the device includes an internal retainer for retaining the tubular member with the internal surface of the trachea adjacent the opening; that the external retainer is a flange, that the internal retainer is a displaceable member, that the displaceable member is a hinged tab, and that the tab is connected with a cord by which the tab can be displaced.

\* \* \* \* \*